United States Patent [19]

Shigeto et al.

[11] Patent Number: 5,391,225
[45] Date of Patent: Feb. 21, 1995

[54] ALKENYLSUCCINI ACID EMULSION SIZING AGENT

[75] Inventors: Hatanaka Shigeto, Kanagawa; Hideto Umekawa, Miyagi, both of Japan

[73] Assignee: Mitsubishi Oil. Co., Ltd., Tokyo, Japan

[21] Appl. No.: 134,904

[22] Filed: Oct. 13, 1993

[30] Foreign Application Priority Data

Oct. 16, 1992 [JP] Japan .................. 4-303174

[51] Int. Cl.$^6$ .................. C09D 7/12; D21H 17/16
[52] U.S. Cl. .................. 106/287.2; 106/219; 106/238; 106/243; 106/285; 162/158; 162/167; 162/169; 162/173; 162/179; 162/180; 524/112
[58] Field of Search .......... 106/219, 238, 243, 285, 106/287.2; 162/167, 169, 173, 179, 180, 158; 524/112

[56] References Cited

U.S. PATENT DOCUMENTS

| | | | |
|---|---|---|---|
| 3,821,069 | 6/1974 | Wurzburg | 162/158 |
| 4,514,229 | 4/1985 | Sato et al. | 106/135 |
| 4,529,447 | 7/1985 | Okada et al. | 106/287.24 |
| 4,533,434 | 8/1985 | Yoshioka et al. | 162/124 |
| 4,673,439 | 6/1987 | Takahashi et al. | 106/287.24 |
| 5,219,912 | 6/1993 | Takahashi et al. | 524/321 |

FOREIGN PATENT DOCUMENTS

| | | |
|---|---|---|
| 0468280 | 1/1992 | European Pat. Off. |
| 2396120 | 1/1979 | France. |
| 58-214598 | 12/1983 | Japan .................. D21H 3/08 |

OTHER PUBLICATIONS

Database WPI. Section Ch. Week 8635 (Jul. 1986).
Database WPI. Section Ch. Week 8613 (Feb. 1986).

*Primary Examiner*—David Brunsman
*Attorney, Agent, or Firm*—Sughrue, Mion, Zinn, Macpeak & Seas

[57] ABSTRACT

An alkenylsuccinic acid emulsion sizing agent, wherein said alkenylsuccinic acid emulsion sizing agent has a solid concentration of at least 25% by weight, and comprises active components comprising an alkenylsuccinic acid present in an amount of at least 50 parts by weight, per 100 parts by weight of the total active components in the alkenylsuccinic acid emulsion sizing agent; and, wherein said alkenylsuccinic acid is obtained by dispersing a product prepared by reacting a branched inner olefin having from 9 to 18 carbon atoms with maleic anhydride in water using an amphoteric acrylamide-series polymer.

19 Claims, No Drawings

ALKENYLSUCCINI ACID EMULSION SIZING AGENT

FIELD OF THE INVENTION

This invention relates to an alkenylsuccinic acid emulsion sizing agent which has a high concentration, good storage stability, and an excellent sizing effect on paper.

BACKGROUND OF THE INVENTION

For a long time, saponified (solution-type) rosin sizing agents have been used in the so-called acidic paper-making process as a paper sizing agent for internal addition such sizing agents being used together with aluminum sulfate. However, at a low addition level, these sizing agents can achieve only a poor sizing effect. Furthermore, in systems having an elevated water temperature or an almost neutral pH range (such as in the expanded use of closed drainage systems) it is known that the sizing effect is deteriorated. In order to overcome these inherent disadvantages of the saponified rosin sizing agents, emulsion sizing agents have been developed. However, at the present time, these emulsion sizing agents are not always satisfactory, since, at a low addition level, they can achieve only a limited sizing effect.

In recent years, sizing agents prepared by alkali-saponifying alkenylsuccinic acids have been employed as a sizing agent which give a good-sizing effect even at a low addition ratio and, thus, compensates for the disadvantages of the above-mentioned rosin sizing agents (e.g., see JP-A-58-214598, wherein the term "JP-A", as used herein, means an "unexamined published Japanese patent application"). However, at a high temperature or in an almost neutral pH range, these sizing agents are disadvantageous in that they suffer from deterioration in the sizing effect in paper-making similar to the saponified rosin sizing agents.

Furthermore, U.S. Pat. No. 3,821,069 discloses a process wherein a mixture of an alkenylsuccinic anhydride blended with an emulsifier is emulsified in a solution of cationized starch or water at a low concentration of from about 0.5 to 3%, and the alkenylsuccinic acid-series emulsion sizing agent thus obtained is used as a sizing agent for neutral paper-making.

The function mechanism of an alkenylsuccinic anhydride in the neutral paper-making process proceeds as follows. The anhydride group of the alkenylsuccinic anhydride is fixed on pulp fibers through a direct reaction with the hydroxyl group of pulp. Thus, the sizing effect is exerted. In the neutral paper-making process, it is, therefore, necessary to add the conventional alkenylsuccinic anhydride as such (i.e., being in the form of an anhydride) to a pulp slurry. However, the alkenylsuccinic anhydride is highly reactive with water too. When the alkenylsuccinic anhydride is preliminarily emulsified and dispersed in water, it would quickly undergo a reaction with water and thus lose its anhydride group. As a result, the alkenylsuccinic anhydride loses its function as a neutral sizing agent. Furthermore, the emulsified state is modified during the process of the conversion of the alkenylsuccinic anhydride into the corresponding alkenylsuccinic acid, thus causing aggregation, precipitation and separation. That is to say, when an emulsion sizing agent comprising an alkenylsuccinic anhydride is used in the form of an aqueous dispersion in a neutral paper-making process, it can be stored for only several hours. It is, therefore, impossible to provide such a sizing agent in the form of a preliminarily emulsified product having a high concentration. Thus, it should be emulsified and dispersed with the use of an emulsifying machine immediately before the paper-making. In addition to this problem in handling, the emulsion sizing agent comprising an alkenylsuccinic anhydride is disadvantageous in that it requires a long rise time for exerting the sizing effect in an acidic region where aluminum sulfate is used as an adhesion promoter and exerts only a poor sizing effect immediately after the completion of the paper-making.

As discussed above, a conventional alkenylsuccinic anhydride emulsion exerts only a poor sizing effect immediately after paper-making in the acidic paper-making process. This is seemingly because this emulsion sizing agent is fixed on pulp fibers as such (i.e., in the form of the acid anhydride) and, therefore, reacts slowly with the pulp in an acidic region. Furthermore, a long time is required for the conversion of the alkenylsuccinic anhydride into the corresponding alkenylsuccinic acid through reaction with water and the subsequent reaction with aluminum sulfate, thus achieving the desired sizing effect. Provided that the alkenylsuccinic anhydride can be emulsified into the alkenylsuccinic acid, the reaction with aluminum sulfate would rapidly proceed and, as a result, an excellent sizing effect might be achieved even in the acidic region.

However, an alkenylsuccinic acid is a highly hydrophilic substance and, therefore, is difficult to emulsify. Thus, it is difficult by conventional techniques to give an emulsion thereof which has a high concentration and can be sustained in a stable state for a long time. When an alkenylsuccinic anhydride is emulsified by a conventional method such as described above, the alkenylsuccinic anhydride reacts with water in the emulsion and changes into the alkenylsuccinic acid, thus giving an emulsion of the alkenylsuccinic acid. During the process of the conversion of the alkenylsuccinic anhydride into the alkenylsuccinic acid, the emulsified state is modified, which makes it impossible to obtain a stable emulsion of the alkenylsuccinic acid. That is to say, even though an emulsion containing alkenylsuccinic anhydride having a high concentration might be temporarily prepared, said alkenylsuccinic anhydride would react with water in the emulsion and change into the alkenylsuccinic acid while simultaneously causing aggregation, precipitation and separation and, therefore, no stable emulsion can be sustained. Thus, it has been thus far impossible to give a highly stable emulsion containing an alkenylsuccinic acid in a high concentration.

SUMMARY OF THE INVENTION

In view of the foregoing, an object of the present invention is to overcome the disadvantages of the above-mentioned saponified alkenylsuccinic acid sizing agents and alkenylsuccinic anhydride emulsion sizing agents by providing a novel emulsion sizing agent of an alkenylsuccinic acid which exerts an excellent sizing effect immediately after paper-making even at a low addition level in a high temperature paper-making process and over a wide pH range and, furthermore, has a high concentration and a good storage stability.

In order to solve the above-mentioned problems and to provide an emulsion sizing agent having the excellent properties of an alkenylsuccinic acid, the present inventors have conducted extensive studies. As a result, they have successfully found that the use of an amphoteric acrylamide-series polymer as an emulsifying dispersant makes it possible to produce an alkenylsuccinic acid emulsion sizing agent having a high concentration and a good storage stability, and the emulsion thus obtained has an excellent storage stability and exerts a remarkable sizing effect, which can not be achieved by conventional saponified alkenylsuccinic acid-series sizing agents, even at a low addition level, in a high temperature paper-making process and in an almost neutral pH range.

Accordingly, the present invention relates to an alkenylsuccinic acid-series emulsion sizing agent, wherein the alkenylsuccinic acid emulsion sizing agent has a solid concentration of at least 25% by weight, and comprises active components comprising an alkenylsuccinic acid present in an amount of at least 50 parts by weight, per 100 parts by weight of the total active components in the alkenylsuccinic acid emulsion sizing agent; and, wherein the alkenylsuccinic acid is obtained by dispersing a product prepared by reacting a branched inner olefin having from 9 to 18 carbon atoms with maleic anhydride in water using an amphoteric acrylamide-series polymer. The term "active component", as used herein, means hydrophobic components capable of exerting sizing performance exemplified by alkenylsuccinic acids as well as those which can be blended therewith such as rosin, rosin derivatives, paraffin wax, tall oil, fatty acids, petroleum resins and petroleum hydrocarbons. The term "solid concentration", as used herein, means the ratio of the components other than water to the whole composition including water.

DETAILED DESCRIPTION OF THE INVENTION

The sizing agent according to the present invention may be produced by any known emulsifying techniques such as phase reversal emulsification or by using a homogenizer. By using a high pressure emulsifier, an alkenylsuccinic acid emulsion having a particularly fine structure and a good stability can be obtained. In this case, a composition containing an alkenylsuccinic acid is molten by heating, and both hot water and an emulsifying dispersant containing an amphoteric acrylamide-series polymer are added thereto. After pre-emulsifying, the mixture is further emulsified in the high pressure emulsifier. The solid concentration of the sizing agent is, preferably, at least 25% by weight, more preferably, at least 30% by weight, in view of transportational cost savings.

As the alkenylsuccinic acid to be used in the present invention, those prepared by reacting an alkenylsuccinic anhydride with an equimolar amount of water may be used. As the alkenylsuccinic anhydride, those obtained through an addition reaction between an olefin and maleic anhydride are usable. As the olefin to be used therefor, branched inner olefins having from 9 to 18 carbon atoms are preferable, since they can achieve excellent sizing effects. Among these branched inner olefins, propylene or butene oligomers are the most preferable since they are not expensive and have excellent sizing effects. In addition, it is possible to use an octene dimer. As the propylene oligomers, their tetramer or pentamer are preferred. As the butene oligomers, their trimers or tetramers are preferred. Although alkenylsuccinic acids obtained from straight-chain olefins are inferior in sizing effect, they may be partly blended with the alkenylsuccinic acids obtained from branched olefins, so long as the effects of the present invention are not deteriorated thereby.

As the amphoteric acrylamide-series polymer to be used in the present invention, those comprising acrylamide and/or methacrylamide as a main monomer together with water-soluble cationic monomer(s) and/or salts thereof and water-soluble anionic monomer(s) and/or salts thereof may be used. An amphoteric acrylamide-series polymer having excellent emulsifying dispersion performance comprises, as essential constituting monomers, (a) from 0.1 to 20% by mol of a water soluble cationic monomer(s) and/or salts thereof; (b) from 0.1 to 30% by mol of a water-soluble anionic monomer(s) and/or salts thereof; and (c) from 50 to 99.8% by mol of acrylamide and/or methacrylamide.

As the water-soluble cationic monomer to be used as component (a), those having a tertiary amino group or a quaternary ammonium group are preferable to those having a primary amino group or a secondary amino group. Examples of a monomer having a tertiary amino group include dimethylaminoethyl (meth)acrylate and dimethylaminopropyl (meth)acrylamide, while examples of a monomer having a quaternary ammonium group include those prepared by quaternarizing these monomers with, for example, methyl chloride.

As the water soluble anionic monomer to be used as component (b), (meth)acrylic acid, maleic acid, itaconic acid, fumaric acid, citraconic acid and salts thereof may be used.

Furthermore, if needed, hydrophobic monomers (such as acrylates and styrene) or cross-linked monomers may each be partly used.

Polymerization can be performed in accordance with a known method, for example, as described in JP-B-1-49839 (the term "JP-B", as used herein, means an "examined Japanese patent publication").

An amphoteric acrylamide-series polymer wherein anion groups have been partly or completely saponified may be used in the present invention.

In the emulsification step, the amphoteric acrylamide-series polymer of the present invention can be used together with other emulsifying dispersants such as other emulsifiers or polymer emulsifying dispersants. Examples of the emulsifiers being usable in this case include: anionic surfactants such as alkylbenzenesulfonic acid salts, polyoxyethylene alkyl ether sulfate salts, polyoxyethylene alkyl phenyl ether sulfate salts, polyoxyethylene aralkyl phenyl ether sulfate salts, alkyl ether sulfate salts, polyoxyethylene alkyl ether phosphates and salts thereof, polyoxyethylene alkyl phenyl ether phosphates and salts thereof, and polyoxyethylene aralkyl phenyl ether phosphates and salts thereof; and, nonionic surfactants such as polyoxyethylene alkyl ethers, polyoxyethylene alkyl phenyl ethers, polyoxyethylene aralkyl phenyl ethers, sorbitan fatty acid esters and polyoxyethylene sorbitan fatty acid esters.

As the polymer emulsifying dispersants, polymers consisting of hydrophilic monomers, copolymers consisting of hydrophilic monomers with hydrophobic monomers, and anionic (co)polymers obtained by partly or completely saponifying the above-mentioned ones may be used. Examples of the hydrophilic monomers include acrylic acid, methacrylic acid, maleic acid, maleic anhydride, itaconic acid and fumaric acid, while examples of the hydrophobic monomers include styrene-series monomers such as styrene and α-methylstyrene, acrylates and methacrylates such as methyl acrylate, methyl methacrylate, ethyl acrylate, ethyl methacrylate, butyl acrylate and butyl methacrylate, (meth)acrylamide and acrylonitrile. Further, polyvinyl alcohol is usable as a polymer emulsifying dispersant.

If desired, the alkenylsuccinic acid may be blended with other hydrophobic substances such as rosin, products obtained by reacting rosin with $\alpha,\beta$-unsaturated polybasic acids, denatured rosins such as disproportionated rosin, polymerized rosin, hydrogenated rosin and a product obtained by reacting rosin with formaldehyde, fatty acids, tall oil, paraffin wax or petroleum hydrocarbons to give active components.

The alkenylsuccinic acid amounts to at least 50 parts by weight, preferably, at least 70 parts by weight, per 100 parts by weight of the total active components. When a hydrophobic substance is used, preferably, the alkenylsuccinic acid comprises from 50 to 95 parts by weight, and the hydrophobic substances are present in an amount of 5 to 50 parts by weight, per 100 parts by weight of the total active components. If the amount of the hydrophobic substance (exclusive of the alkenylsuccinic acid) is greater than 50 parts by weight, per 100 parts by weight of the total active components, the sizing effect is deteriorated.

When the alkenylsuccinic acid is replaced with an alkenylsuccinic anhydride and the emulsification is performed in the same manner as the one described above, an aqueous emulsion containing the alkenylsuccinic anhydride can be obtained. In this case, the alkenylsuccinic anhydride reacts with water in the emulsion and thus changes into the corresponding alkenylsuccinic acid within one or two days. When the amphoteric acrylamide-series polymer is used as an emulsifying dispersant as in the present invention, the conversion of the alkenylsuccinic anhydride into the alkenylsuccinic acid causes no change in the emulsified state and no aggregation, precipitation or separation is observed. Thus, the sizing agent of the present invention containing the alkenylsuccinic acid in a stable form can be obtained. In this case, the alkenylsuccinic anhydride may be emulsified alone. However, a sizing agent having an improved stability can be obtained by blending said alkenylsuccinic anhydride with a hydrocarbon resin free from any acid group as described in U.S. Pat. No. 5,219,912.

The composition ratio of the amphoteric acrylamide-series polymer to the alkenylsuccinic acid ranges, preferably, from 0.5 to 20 parts by weight, more preferably, from 1 to 15 parts by weight, per 100 parts by weight of the alkenylsuccinic acid. When rosin, rosin derivatives, fatty acids, tall oil, paraffin wax or petroleum hydrocarbons are to be blended in addition to the alkenylsuccinic acid, the amphoteric acrylamide-series polymer may be used in an amount of from 0.5 to 20 parts by weight, preferably, from 1 to 15 parts by weight, per 100 parts by weight of the total content of the active components in the alkenylsuccinic acid emulsion sizing agent.

Further, denatured products of alkenylsuccinic acids such as alkali metal salts, esters, imides or amides may be used in the present invention, though they scarcely contribute to the achievement of the sizing effect.

Similar to the conventional rosin-series sizing agents, the sizing agent according to the present invention may be added at an arbitrary stage before the completion of the paper-making procedure. For example, aluminum sulfate is added before or after the addition of the sizing agent of the present invention to a pulp slurry during or after the beating step to thereby adjust the slurry to pH 4.0 to 7.0. Thus, the sizing agent can be fixed on the pulp. During the application, the sizing agent of the present invention may be used together with the conventional rosin-series sizing agents, petroleum rosin sizing agents or other sizing agents at an arbitrary ratio.

In the case of inner addition sizing, the sizing agent of the present invention may be added in an amount of from 0.01 to 5.0% by weight, preferably, from 0.05 to 3.0% by weight, based on the total weight of the dry pulp.

To further illustrate the present invention in greater detail, the following Examples and Comparative Examples will be given. However, it is to be understood that the present invention is not restricted thereto. Unless otherwise noted, all "parts" given in these examples are by weight.

PREPARATION OF AMPHOTERIC ACRYLAMIDE POLYMER

Reference Example 1

In a four-neck separable flask (1 liter) provided with a stirrer, a thermometer, a condenser and an $N_2$-inlet, were weighed 7.8 g (corresponding to 3.8 mol %) of dimethylaminopropylacrylamide, 2.9 g (corresponding to 1.9 mol %) of maleic acid, 89.3 g (corresponding to 94.4 mol %) of acrylamide and 556 g of distilled water. Then, 2.8 g of phosphoric acid was added thereto to thereby adjust the mixture to Ph 4.0. After adding 0.04 g of 2-mercaptoethanol and replacing with $N_2$, the mixture was heated to 70° C. under stirring. Then, 0.5 g of ammonium persulfate was added and polymerization was thus initiated. The mixture was maintained at the same temperature for 2 hours. The polymer thus obtained had a viscosity of 8,700 cps at 25° C. and a solid concentration of 16.6% by weight. When ionic groups in the polymer were determined by colloidal titration, it was determined that both cationic and anionic groups had been introduced into the polymer at the proper ratios.

Reference Example 2

To the same flask as used in Reference Example 1 were fed 23.6 g (corresponding to 12.3 mol %) of dimethylaminopropylacrylamide, 10.8 g (corresponding to 12.2 mol %) of acrylic acid, 65.8 g (corresponding to 75.5 mol %) of acrylamide and 561 g of distilled water, followed by performing the same procedure (including the amount of the catalyst) as described in Reference Example 1. The polymer thus obtained had a viscosity of 9,600 cps at 25° C. and a solid concentration of 16.7% by weight. When ionic groups in the polymer were determined by colloidal titration, it was determined that both cationic and anionic groups had been introduced into the polymer at the proper ratios.

Reference Example 3

In the same flask as used in Reference Example 1 were weighed 36.2 g (corresponding to 8.2 mol %) of methacryloyloxyethyltrimethylammonium chloride at an active component content of 80%, 10.1 g (corresponding to 8.3 mol %) of acrylic acid, 100.9 g (corresponding to 83.5 mol %) of acrylamide and 825.4 g of distilled water. Then, 7.2 g of 40% by weight NaOH was added thereto to thereby adjust the mixture to pH 4.0. After adding 0.07 g of 2-mercaptoethanol and replacing with $N_2$, the mixture was heated to 70° C. under stirring. Then, 0.7 g of ammonium persulfate was added and polymerization was thus initiated. The mixture was maintained at the same temperature for 2 hours. The polymer thus obtained had a viscosity of 15,000 cps at 25° C. and a solid concentration of 15.0% by weight. When ionic groups in the polymer were determined by colloidal titration, it was determined that both cationic and anionic groups had been introduced into the polymer at the proper ratios.

Storage Stability Test 25 g portions of the alkenylsuccinic acid-series emulsion sizing agents prepared by the methods described in Examples 1 to 6, the commercially available sizing agent of Comparative Example 1 and the alkenylsuccinic acid-series emulsion sizing agents prepared by the methods described in Comparative Examples 3, 4, 5 and 6 were packed in 50 ml glass bottles and allowed to stand at room temperature (25° C.). Then, the stability of each sample was observed with the eye after 1, 7 and 60 days. A sample having a poor stability suffered from the separation and precipitation of oily matter at the surface of the liquid or on the bottom of the bottle. The products of Comparative Examples 2 and 7 were not subjected to this storage stability test since they were not emulsion sizing agents but saponified sizing agents.

Sizing Effect Test

Bleached kraft pulp (LBKP) was diluted with tap water to a pulp concentration of 2.5% and beaten with a beater to Canadian freeness of about 450 ml. The pulp slurry thus obtained was then diluted with tap water at 50° C. to give a 2.0% by weight slurry, and 1.0% by weight, based on the pulp, of aluminum sulfate was added thereto. Next, the slurry was diluted with water (pH 4.5, 50° C.) to a concentration of 0.5% by weight, and the sizing agents of Examples 1 to 6 and Comparative Examples 1 to 7 were added thereto at a ratio of 0.3% by weight based on the pulp, followed by paper-making with a TAPPI standard machine (paper weight: 60 g/m$^2$). The moist paper thus obtained was then pressed and dried in a conventional manner. The obtained paper was conditioned immediately after drying in a thermo-hygrostat at a temperature of 20° C. under a relative humidity of 65% for one day. Then, the sizing effect was determined by Stöckigt's method in accordance with JIS P 8122.

To effect a higher-pH paper-making test, paper samples prepared by adding 0.7% by weight, based on the pulp, of aluminum sulfate and adjusting the pH values of the diluting water and paper-making water to 6.0 were also evaluated. The sizing agents of Examples 1 to 6 and those of Comparative Example 5 were used in the test 10 days after emulsifying. On the other hand, the alkenylsuccinic anhydride emulsion sizing agents of Comparative Examples 3, 4 and 6 were used in the test immediately after emulsifying since they are poor in storage stability and could not be maintained in a satisfactorily emulsified state 10 days after emulsifying.

EXAMPLE 1

An alkenylsuccinic anhydride obtained via an addition reaction between a propylene oligomer (average carbon atom number: 15) and maleic anhydride was reacted with an equimolar amount of water to thereby give an alkenylsuccinic acid. 100 parts of this alkenylsuccinic acid was heated to 90° C. and 30 parts (5 parts of solid matter per 100 parts of the alkenylsuccinic acid) of the amphoteric acrylamide-series polymer of Reference Example 1 and 170 parts of hot water were added thereto, followed by mixing. Next, the obtained emulsion was homogenized by passing through a piston type high-pressure emulsifier (manufactured by APV-Gaulin Co.) under a pressure of 300 kg/cm$^2$ twice. Then, it was rapidly cooled to room temperature to thereby give an oil-in-water type emulsion having a total solid content of 35% by weight.

EXAMPLE 2

An alkenylsuccinic anhydride obtained via an addition reaction between a propylene oligomer (average carbon atom number: 18) and maleic anhydride was reacted with an equimolar amount of water to thereby give an alkenylsuccinic acid. 80 parts of this alkenylsuccinic acid and 20 parts of fumarated rosin (modified rosin with fumaric acid) were heated to 90° C. and 18 parts (3 parts of solid matter per 100 parts of the active components) of the amphoteric acrylamide-series polymer of Reference Example 2 and a solution (heated to 90° C.) of 5 parts of polyvinyl alcohol (tradename: Poval PVA-217, manufactured by Kuraray Co., Ltd., degree of polymerization: ca. 1,700, degree of saponification: 88 mol %) in 147 parts of water were added thereto, followed by mixing. Next, the obtained mixture was emulsified by stirring in a homomixer (Model TK, manufactured by Tokushu Kika Kogyo K. K.) at 10,000 rpm for 2 minutes to thereby give an oil-in-water type emulsion having a total solid content of 40% by weight.

EXAMPLE 3

An alkenylsuccinic anhydride obtained via an addition reaction between a propylene oligomer (average carbon atom number: 12) and maleic anhydride was reacted with an equimolar amount of water to thereby give an alkenylsuccinic acid. 70 parts of this alkenylsuccinic acid was mixed with 30 parts of tall oil (tradename: SR-30, manufactured by Harima Chemicals, Inc.) at 70° C. Then, 47 parts (7 parts of solid matter per 100 parts of the active components) of the amphoteric acrylamide-series polymer of Reference Example 3 and 176 parts of hot water were added thereto, followed by mixing. Next, the obtained emulsion was homogenized by passing through a piston type high-pressure emulsifier (manufactured by APV-Gaulin Co.) under a pressure of 300 kg/cm$^2$ twice. Then, it was rapidly cooled to room temperature to thereby give an oil-in-water type emulsion having a total solid content of 35% by weight.

EXAMPLE 4

To 80 parts of an alkenylsuccinic anhydride prepared via an addition reaction of an n-butene oligomer (average carbon atom number: 16) with maleic anhydride, was added 20 parts of an aromatic methylene resin (tradename: Oligotech 1300, manufactured by Mitsubishi Oil Co.f Ltd., average molecular weight: 700) at 80° C. Then, 3 parts of polyoxyethylene (degree of polymerization: 17) nonylphenyl ether phosphate, 2 parts of polyoxyethylene (degree of polymerization: 4) nonylphenyl ether sulfate ammonium and 30 parts (5 parts of solid matter per 100 parts of the active component) of the amphoteric acrylamide-series polymer of Reference Example 1 were further added thereto, followed by mixing. 140 parts of hot water was slowly added thereto, and the mixture was subjected to phase reversal emulsification to thereby give an oil-in-water type emulsion having a total solid content of 40% by weight.

EXAMPLE 5

An alkenylsuccinic anhydride obtained via an addition reaction between a propylene oligomer (average carbon atom number: 15) and maleic anhydride was reacted with an equimolar amount of water to thereby give an alkenylsuccinic acid. 90 parts of this alkenylsuccinic acid and 10 parts of gum rosin were mixed at 80° C. and 67 parts (10 parts of solid matter per 100 parts of the active components) of the amphoteric acrylamide-series polymer of Reference Example 3 was added thereto. Further, a solution (heated to 90 ° C.) of 3 parts of polyvinyl alcohol having the block copolymerization-type (tradename: Poval PVA-217E, manufactured by Kuraray Co., Ltd., degree of polymerization: ca. 1,700, degree of saponification: 88 mol %) in 113 parts of water was added thereto, followed by mixing. Next, the obtained mixture was homogenized by passing through a piston-type high-pressure emulsifier (manufactured by APV-Gaulin Co.) under a pressure of 300 kg/cm$^2$ twice. Then, it was rapidly cooled to room temperature to thereby give an oil-in-water type emulsion having a total solid content of 40% by weight.

EXAMPLE 6

An alkenylsuccinic anhydride obtained via an addition reaction between an olefin mixture (1:1 parts by weight) comprising a propylene oligomer (average carbon atom number: 9) with an n-butene oligomer (average carbon atom number: 12) and maleic anhydride was reacted with an equimolar amount of water to thereby give an alkenylsuccinic acid. 80 parts of this alkenylsuccinic acid and 20 parts of an aromatic methylene resin (tradename: Oligotech 1300, manufactured by Mitsubishi Oil Co., Ltd., average molecular weight: 700) were mixed at 90° C. and 78 parts (13 parts of solid matter per 100 parts of the active components) of the amphoteric acrylamide-series polymer of Reference Example 1 and 200 parts by weight of water were added thereto. Next, the obtained mixture was homogenized by passing through a piston type high-pressure emulsifier (manufactured by APV-Gaulin Co.) under a pressure of 300 kg/cm$^2$ twice. Then, it was rapidly cooled to room temperature to thereby give an oil-in-water type emulsion having a total solid content of 30% by weight.

Comparative Example 1

A commercially available emulsion sizing agent (OT-500J, manufactured by Dick Hercules Co.), which was prepared by emulsifying components comprising fumarated rosin (modified rosin with fumaric acid) with a polymer emulsifying dispersant and had a solid content of 50%, was used.

Comparative Example 2

A commercially available emulsion sizing agent (PF Size 800L, manufactured by Misawa Ceramic Chemical K. K.), which was prepared by saponifying components comprising maleated rosin (modified rosin with maleic anhydride) with sodium hydroxide and had a solid content of 50%, was used.

Comparative Example 3

To 100 parts of an alkenylsuccinic anhydride obtained via an addition reaction between a propylene oligomer (average carbon atom number: 15) and maleic anhydride, was added 5 parts of polyoxyethylene (degree of polymerization: 13) nonylphenyl ether, followed by well stirring at 50° C. One part of the resulting mixture was mixed with 99 parts of water and emulsified by stirring in a homomixer at 10,000 rpm for 1 minute. Thus, an oil-in-water type emulsion having a total solid content of 1% by weight was obtained.

Comparative Example 4

To 100 parts of an alkenylsuccinic anhydride obtained via an addition reaction between a straight-chain inner olefin (average carbon atom n-umber: 16) and maleic anhydride, was added 5 parts of polyoxyethylene (degree of polymerization: 13) nonylphenyl ether, followed by well stirring at 50° C. One part of the resulting mixture was mixed with 99 parts of water and emulsified by stirring in a homomixer at 10,000 rpm for 1 minute. Thus, an oil-in-water type emulsion having a total solid content of 1% by weight was obtained.

Comparative Example 5

To 80 parts of an alkenylsuccinic anhydride obtained via an addition reaction between a straight-chain inner olefin (average carbon atom number: 16) and maleic anhydride, was added 20 parts of a commercially available aromatic methylene resin (tradename: Oligotech 1300, manufactured by Mitsubishi Oil Co., Ltd., average molecular weight: 700). Further, 4 parts of polyoxyethylene (degree of polymerization: 17) nonylphenyl ether phosphate, 3 parts of polyoxyethylene (degree of polymerization: 4) nonylphenyl ether sulfate ammonium and 2 parts of oleic acid were added thereto. Then, a solution of 10 parts of anion-modified polyvinyl alcohol (tradename: Gosenal T-350, manufactured by The Nippon Synthetic Chemical Industry, Co., Ltd., degree of polymerization: ca. 1,500, degree of saponification: 94 mol %) dissolved in 180 parts of water was slowly added thereto and the mixture was subjected to phase reversal emulsification. Thus, an oil-in-water type emulsion having a total solid content of 40% by weight was obtained.

Comparative Example 6

An alkenylsuccinic anhydride obtained via an addition reaction between a propylene oligomer (average carbon atom number: 15) and maleic anhydride was reacted with an equimolar amount of water to thereby give an alkenylsuccinic acid. 100 parts of this alkenylsuccinic acid was heated to 90° C. and a solution (heated to 90° C.) of 5 parts of polyoxyethylene (degree of polymerization: 13) nonylphenyl ether dissolved in 155 parts of water was added thereto. Subsequently, the obtained emulsion was homogenized by passing through a piston-type high-pressure emulsifier (manufactured by APV-Gaulin Co.) under a pressure of 300 kg/cm$^2$ twice. Then, it was rapidly cooled to room temperature to thereby give an oil-in-water type emulsion having a total solid content of 40% by weight.

Comparative Example 7

To 60 parts of an alkenylsuccinic anhydride obtained via an addition reaction between a propylene oligomer (average carbon atom number: 12) and maleic anhydride, was added an aqueous solution of 26 parts of potassium hydroxide in 126 parts of water. The mixture was maintained at 90 to 100 ° C. under stirring. After 3 hours, it was cooled to room temperature and, thus, an alkenylsuccinic acid-series sizing agent having a total solid content of 40% by weight was obtained.

TABLE 1

Results of Storage Stability Test

| | Storage Time (day) | | |
|---|---|---|---|
| | 1 | 7 | 60 |
| Ex. 1 | no precipitate | no precipitate | trace precipitate |
| Ex. 2 | " | " | " |
| Ex. 3 | " | " | no precipitate |
| Ex. 4 | " | " | " |
| Ex. 5 | " | " | " |
| Ex. 6 | " | " | " |
| C. Ex. 1 | no precipitate | no precipitate | trace precipitate |
| C. Ex. 2 | — | — | — |
| C. Ex. 3 | much precipitate | much precipitate | much precipitate |
| C. Ex. 4 | much precipitate | " | " |
| C. Ex. 5 | no precipitate | no precipitate | trace precipitate |
| C. Ex. 6 | much precipitate | much precipitate | much precipitate |
| C. Ex. 7 | — | — | — |

TABLE 2

Results of Sizing Effect Test

Stöckigt Sizing Degree (sec)

| | Aluminum sulfate 1.0% Water for paper-making (pH 4.5) | | Aluminum sulfate 0.7% Water for paper-making (pH 6.0) | |
|---|---|---|---|---|
| | Immediately after drying | After conditioning for 1 day | Immediately after drying | After conditioning for 1 day |
| Ex. 1 | 20 | 20 | 13 | 14 |
| Ex. 2 | 18 | 18 | 15 | 15 |
| Ex. 3 | 19 | 20 | 15 | 15 |
| Ex. 4 | 19 | 19 | 14 | 15 |
| Ex. 5 | 21 | 22 | 16 | 17 |
| Ex. 6 | 21 | 21 | 14 | 15 |
| C. Ex. 1 | 14 | 15 | 8 | 9 |
| C. Ex. 2 | 4 | 8 | 2 | 5 |
| C. Ex. 3 | 0 | 3 | 1 | 5 |
| C. Ex. 4 | 0 | 16 | 2 | 20 |
| C. Ex. 5 | 6 | 7 | 5 | 5 |
| C. Ex. 6 | 2 | 6 | 4 | 8 |
| C. Ex. 7 | 12 | 12 | 6 | 7 |

Compared with conventional alkenylsuccinic anhydride emulsion sizing agents, the alkenylsuccinic acid-series emulsion sizing agent of the present invention is excellent in storage stability at a high concentration and exhibits an excellent sizing effect immediately after paper-making. Further, compared with saponified alkenylsuccinic acid-series sizing agents, the alkenylsuccinic acid-series emulsion sizing agent of the present invention suffers from only a slight deterioration in the sizing effect over a wide pH range even in a high-temperature paper-making process.

While the invention has been described in detail and with reference to specific embodiments thereof, it will be apparent to one skilled in the art that various changes and modifications can be made therein without departing from the spirit and scope thereof.

What is claimed is:

1. An alkenylsuccinic acid emulsion sizing agent, wherein said alkenylsuccinic acid emulsion sizing agent has a solid concentration of at least 25% by weight, and comprises active components comprising an alkenylsuccinic acid present in an amount of at least 50 parts by weight, per 100 parts by weight of the total active components in the alkenylsuccinic acid emulsion sizing agent; and, wherein said alkenylsuccinic acid is obtained by dispersing a product prepared by reacting a branched inner olefin having from 9 to 18 carbon atoms with maleic anhydride in water using an amphoteric acrylamide-series polymer comprising (a) at least one of a water-soluble cationic monomer and a salt thereof, (b) at least one of a water-soluble anionic monomer and a salt thereof, and (c) at least one of acrylamide and methacrylamide.

2. An alkenylsuccinic acid emulsion sizing agent as claimed in claim 1, wherein said active components comprise from 50 to 95 parts by weight of said alkenylsuccinic acid and further comprise from 5 to 50 parts by weight of at least one component selected from the group consisting of rosin, rosin compounds, fatty acid, petroleum resins and petroleum hydrocarbons.

3. An alkenylsuccinic acid emulsion sizing agent as claimed in claim 2, wherein said branched inner olefin is an oligomer of propylene or butene.

4. An alkenylsuccinic acid emulsion sizing agent as claimed in claim 3, wherein said amphoteric acrylamide-series polymer consists of (a) from 0.1 to 20 mol % of at least one of a water-soluble cationic monomer and a salt thereof; (b) from 0.1 to 30 mol % of at least one of a water-soluble anionic monomer and a salt thereof; and (c) from 50 to 99.8 mol % of at least one of acrylamide and methacrylamide.

5. An alkenylsuccinic acid emulsion sizing agent as claimed in claim 3, wherein said amphoteric acrylamide-series polymer is present in an amount of from 1 to 15 parts by weight, per 100 parts by weight of the total active components in the alkenylsuccinic acid emulsion sizing agent.

6. An alkenylsuccinic acid emulsion sizing agent as claimed in claim 2, wherein said amphoteric acrylamide-series polymer consists of (a) from 0.1 to 20 mol % of at least one of a water-soluble cationic monomer and a salt thereof; (b) from 0.1 to 30 mol % of at least one of a water-soluble anionic monomer and a salt thereof; and (c) from 50 to 99.8 mol % of at least one of acrylamide and methacrylamide.

7. An alkenylsuccinic acid emulsion sizing agent as claimed in claim 2, wherein said amphoteric acrylamide-series polymer is present in an amount of from 1 to 15 parts by weight, per 100 parts by weight of the total active components in the alkenylsuccinic acid emulsion sizing agent.

8. An alkenylsuccinic acid emulsion sizing agent as claimed in claim 1, wherein said branched inner olefin is an oligomer of propylene or butene.

9. An alkenylsuccinic acid emulsion sizing agent as claimed in claim 8, wherein said amphoteric acrylamide-series polymer consists of (a) from 0.1 to 20 mol % of at least one of a water-soluble cationic monomer and a salt thereof; (b) from 0.1 to 30 mol % of at least one of a water-soluble anionic monomer and a salt thereof; and (c) from 50 to 99.8 mol % of at least one of acrylamide and methacrylamide.

10. An alkenylsuccinic acid emulsion sizing agent as claimed in claim 8, wherein said amphoteric acrylamide-series polymer is present in an amount of from 1 to 15 parts by weight, per 100 parts by weight of the total active components in the alkenylsuccinic acid emulsion sizing agent.

11. An alkenylsuccinic acid emulsion sizing agent as claimed in claim 1, wherein said amphoteric acrylamide-series polymer consists of (a) from 0.1 to 20 mol % of at least one of a water-soluble cationic monomer and a salt thereof; (b) from 0.1 to 30 mol % of at least one of a water-soluble anionic monomer and a salt thereof; and (c) from 50 to 99.8 mol % of at least one of acrylamide and methacrylamide.

12. An alkenylsuccinic acid emulsion sizing agent as claimed in claim 11, wherein said water-soluble cationic monomer is selected from the group consisting of a tertiary amino group and a quaternary ammonium group, and said water-soluble anionic monomer is selected from the group consisting of a (meth)acrylic acid, maleic acid, itaconic acid, fumaric acid, citraconic acid and salts thereof.

13. An alkenylsuccinic acid emulsion sizing agent as claimed in claim 1, wherein said amphoteric acrylamide-series polymer is present in an amount of from 1 to 15 parts by weight, per 100 parts by weight of the total active components in the alkenylsuccinic acid emulsion sizing agent.

14. A method for preparing an alkenylsuccinic acid emulsion sizing agent, wherein said alkenylsuccinic acid emulsion sizing agent has a solid concentration of at least 25% by weight, and comprises active components comprising an alkenylsuccinic acid present in an amount of at least 50 parts by weight, per 100 parts by weight of the total active components in the alkenylsuccinic acid emulsion sizing agent; and, wherein said alkenylsuccinic acid is prepared by dispersing a product prepared by reacting a branched inner olefin having from 9 to 18 carbon atoms with maleic anhydride in water using an amphoteric acrylamide-series polymer comprising (a) at least one of a water-soluble cationic monomer and a salt thereof, (b) at least one of a water-soluble anionic monomer and a salt thereof, and (c) at least one of acrylamide and methacrylamide.

15. The method for preparing an alkenylsuccinic acid emulsion sizing agent of claim 14, wherein said active components comprise from 50 to 95 parts by weight of said alkenylsuccinic acid and further comprises from 5 to 50 parts by weight of at least one component selected from the group consisting of rosin, rosin compounds, fatty acid, petroleum resins, and petroleum hydrocarbons.

16. The method of preparing an alkenylsuccinic acid emulsion sizing agent of claim 15, wherein said branched inner olefin is an oligomer of propylene or butene.

17. The method for preparing an alkenylsuccinic acid emulsion sizing agent of claim 15, wherein said amphoteric acrylamide-series polymer consists of (a) from 0.1 to 20 mol % of at least one of a water-soluble cationic monomer and a salt thereof; (b) from 0.1 to 30 mol % of at least one of a water-soluble anionic monomer and a salt thereof; and (c) from 50 to 99.8 mol % of at least one of acrylamide and methacrylamide.

18. The method for preparing an alkenylsuccinic acid emulsion sizing agent of claim 14, wherein said branched inner olefin is an oligomer of propylene or butene.

19. The method for preparing an alkenylsuccinic acid emulsion sizing agent of claim 14, wherein said amphoteric acrylamide-series polymer consists of (a) from 0.1 to 20 mol % of at least one of a water-soluble cationic monomer and a salt thereof; (b) from 0.1 to 30 mol % of at least one of a water-soluble anionic monomer and a salt thereof; and (c) from 50 to 99.8 mol % of at least one of acrylamide and methacrylamide.

* * * * *